(12) United States Patent
Lee et al.

(10) Patent No.: US 8,505,819 B2
(45) Date of Patent: Aug. 13, 2013

(54) METHODS OF INCREASING CODING INFORMATION FOR BIOSENSORS AND DEVICES FOR SAME

(75) Inventors: Cheng-Che Lee, Hsin-chu (TW); Wen-Hai Tsai, Taipei (TW); Keng-Hao Chang, Taichung (TW); Chiu-Chin Yang, Hsin-chu (TW); Waken Chen, Hsin-chu (TW); Jih-Hsin Yeh, Taipei (TW)

(73) Assignee: Tyson Bioresearch, Inc., Chu-Nan (TW)

( * ) Notice: Subject to any disclaimer, the term of this patent is extended or adjusted under 35 U.S.C. 154(b) by 0 days.

(21) Appl. No.: 13/281,461

(22) Filed: Oct. 26, 2011

(65) Prior Publication Data

US 2012/0104096 A1    May 3, 2012

Related U.S. Application Data

(60) Provisional application No. 61/408,569, filed on Oct. 29, 2010.

(51) Int. Cl.
*G06K 5/00* (2006.01)

(52) U.S. Cl.
USPC .......................................... 235/437; 235/375

(58) Field of Classification Search
USPC ................. 235/437, 449, 492, 438, 375, 380, 235/472.01
See application file for complete search history.

(56) References Cited

U.S. PATENT DOCUMENTS

| 7,988,917 | B2 * | 8/2011 | Roesicke et al. | 422/82.01 |
| 2004/0054263 | A1 | 3/2004 | Moerman et al. | |
| 2007/0093717 | A1 | 4/2007 | Nagar et al. | |
| 2007/0237678 | A1 * | 10/2007 | Roesicke et al. | 422/82.01 |
| 2010/0161240 | A1 * | 6/2010 | Tseng | 702/22 |
| 2011/0119081 | A1 | 5/2011 | Vespasiani | |
| 2012/0150448 | A1 * | 6/2012 | Hurd et al. | 702/19 |

* cited by examiner

*Primary Examiner* — Thien M Le
(74) *Attorney, Agent, or Firm* — Eastwind Consultants Co., Ltd.; Jenny Chen (57) ABSTRACT

The present invention discloses a biological measuring device with auto coding capabilities. In accordance with one embodiment of the present invention, the biological measuring device with auto coding capabilities includes a test strip having a substrate and at least a first contact pad and a second contact pad provided on the substrate; and a code reader having at least a first metal pin and a second metal pin to couple to the first contact pad and the second contact pad to obtain coding information associated with the test strip, wherein the code reader is capable of reading the coding information based on a movement of the test strip before the test strip is placed still in relation to the code reader for a proper reading of a sample.

38 Claims, 8 Drawing Sheets

METHODS OF INCREASING CODING INFORMATION FOR BIOSENSORS AND DEVICES FOR SAME

CROSS-REFERENCE TO RELATED APPLICATIONS

This application is related to and claims priority to U.S. provisional patent application, U.S. Provisional Application No. 61/408,569, filed on Oct. 29, 2010, by the applicants Cheng-Che Lee, Wen-Hai Tsai, Keng-Hao Chang, Chiu-Chin Yang, Waken Chen, and Jih-Hsin Yeh, entitled "Biosensor and Test Strip and Methods of Manufacturing Same."

FIELD OF THE INVENTION

The present invention relates to biosensors and test strips for same; in particular, the present invention relates to methods of increasing coding information for biosensors and devices for same.

BACKGROUND OF THE INVENTION

Electrochemical measuring devices have been commonly used to determine the concentration of analytes in body fluids. For example, in blood-glucose testing, the test strip may be inserted into a glucose meter, and then a blood sample may be dropped at a measuring end of a test strip that is applied with an enzyme to determine the concentration of glucose in the blood sample.

In the conventional art, the test strip is provided with a working electrode and a reference electrode to form a reaction region. The reaction region is applied with the enzyme so that when a test sample reacts with the enzyme, a chemical response is generated. When in use, the test strip is inserted in the glucose meter so that the glucose meter can read the chemical response in order to calculate the concentration of glucose in the blood sample.

However, as a result of variances in manufacturing of the test strips, calibration is needed before a particular batch of the test strips may be used with the glucose meter to obtain accurate test results. In the conventional art, the test strips are provided with a number of contact pads. These contact pads are used to couple with metal pins provided on a semiconductor chip within the glucose meters to generate electrical current, which in turn produces electrical responses readable by the glucose meters. To compensate for the manufacturing variations, the contact pads on the test strips are encoded with calibration information that may be assigned for use in computing the test results.

One common problem in the conventional art is the amount of coding information that can be encoded in the contact pads for calibration purpose. As an example, a chip with eight pins provided within the conventional glucose meter can correspond to a test strip with eight contact pads. A common arrangement of the eight contact pads may be 2 rows of 4 contact pads at one end of any given test strip. In the conventional art, there are at least a working electrode and a reference electrode to connect with contact pads. Then, depending on the status of electrical conductivity between any contact pads and common pad well know by the art, a logic value of 1 or 0 is assigned, thereby yielding a maximum of 32 ($=2^5$) codes to be used for auto-calibration purpose. Such limitation hinders the optimal use of the glucose meter and test strips.

Therefore, what is needed is a method of increasing the number of auto-calibration codes without changing the existing structure and configuration of the glucose meter and the test strip and device for same.

What is also needed is a method of verifying the auto-calibration codes to increase the accuracy when using the glucose meter in combination with the test strip.

SUMMARY OF THE INVENTION

In light of the drawbacks of the current art, one aspect of the present invention is to provide a biological measuring device with auto coding capabilities. In accordance with one embodiment of the present invention, the biological measuring device with auto coding capabilities may include a test strip having a substrate and at least a first contact pad and a second contact pad provided on the substrate; and a code reader having at least a first metal pin and a second metal pin to couple to the first contact pad and the second contact pad to obtain coding information associated with the test strip, wherein the code reader may be capable of reading the coding information based on a movement of the test strip before the test strip is placed still in relation to the code reader for a proper reading of a sample.

Another aspect of the present invention is to provide a biological measuring device adapted for use with a test strip. In one embodiment of the present invention, the test strip may have at least a first contact pad and a second contact pad. The biological measuring device of the present invention may include a code reader having at least a first metal pin and a second metal pin, wherein the code reader may be capable of reading coding information associated with the test strip based on a movement of the test strip before the test strip is placed still in relation to the code reader for a proper reading of a sample.

Yet another aspect of the present invention is to provide a test strip adapted for use with a biological measuring device. The biological measuring device of the present invention may include a code reader having at least a first metal pin and a second metal pin. The test strip of the present invention may include a substrate and a reaction region formed by at least a first electrode and a second electrode, such as a working electrode, a counter electrode, and a reference electrode provided on the substrate at one end. The reaction region may be applied with an enzyme so that an electrical response is generated when the enzyme and a test sample form a chemical reaction. The test strip of the present invention may include at least a first contact pad and a second contact pad provided on the substrate at the other end to couple to the first and second metal pins to output coding information associated with the test strip, wherein a length of the first or second contact pad may determine a movement of the test strip before the test strip is placed still in relation to the code reader for a proper reading of the test sample.

Yet another aspect of the present invention is to provide a method of reading coding information associated with a test strip adapted for use with a biological measuring device. The test strip of the present invention may have a substrate and at least a first contact pad and a second contact pad provided on the substrate. The biological measuring device of the present invention may include a code reader having at least a first metal pin and second metal pin. The method of the present invention may include inserting the test strip into the code reader; and reading the coding information based on a movement of the test strip before the test strip is placed still in relation to the code reader for a proper reading of a sample, wherein the movement may include an open circuit movement and a closed circuit movement.

Yet another aspect of the present invention is to provide a method of verifying coding information associated with a test strip adapted for use with a biological measuring device. The test strip of the present invention may have a substrate and a plurality of contact pads provided on the substrate. The biological measuring device of the present invention may include a code reader having a plurality of metal pins corresponding to the plurality of contact pads. The method of the present invention may include assigning a parity bit to one of the plurality of contact pads; determining the coding information by counting the number of a logical value generated when the plurality of contact pads are electrically coupled to the plurality of corresponding metal pins; comparing the number of the logical value against a predetermined number for the logical value, and if the number of the logical value matches the predetermined number for the logical value, then the coding information is correct.

Yet another aspect of the present invention is to provide a test strip adapted for use with a biological measuring device. The biological measuring device of the present invention may include a code reader having a plurality of metal pins. The test strip of the present invention may include a substrate; a reaction region formed by at least a first electrode and a second electrode, such as a working electrode, a counter electrode, and a reference electrode provided on the substrate at one end. The reaction region may be applied with an enzyme so that an electrical response is generated when the enzyme and a test sample form a chemical reaction. The test strip of the present invention may also include a plurality of contact pads provided on the substrate, wherein a first and second contact pads of the plurality of contact pads are provided on the substrate at the other end to couple to a respective metal pin to output coding information associated with the test strip, and wherein a third contact pad of the plurality of contact pads is assigned with a parity bit to verify the coding information.

Yet another aspect of the present invention is to provide a biological measuring device adapted for use with a test strip, wherein the test strip may have at least a first, a second and a third contact pads. The device of the present invention may include a code reader having at least a first metal pin and a second metal pin, wherein the code reader may be capable of reading coding information associated with the test strip based on a movement of the test strip before the test strip is placed still in relation to the code reader for a proper reading of a sample, and wherein the code reader may verify the coding information using a parity bit assigned to the third contact pad provided on the test strip.

DETAILED DESCRIPTION OF THE INVENTION

Reference will now be made in detail to the embodiments of the present invention. Examples of embodiments are illustrated in the accompanying drawings, wherein like reference numbers refer to like elements throughout the specification.

The present invention discloses methods of increasing coding information associated with a test strip adapted for use with a biological measuring device as well as devices and test strips for same. In accordance with one embodiment of the present invention, the biological measuring device may be capable of reading coding information associated with the test strip based on a movement of the test strip before the test strip is placed still in relation to the code reader provided within the biological measuring device for a proper reading of a sample. That is, the biological measuring device of the present invention may be capable of reading coding information associated with the test strip based on a movement of the test strip as it enters into the biological measuring device and becomes electrically coupled with a code reader provided with in the biological measuring device. As such, in addition to reading the coding information associated with the test strip when the test strip is properly set still within the code reader, the biological measuring device of the present invention may read further coding information associated with the test strip as the test strip is pushed into the code reader, thereby increasing the auto-coding capabilities of the biological measuring device.

Figure 1:
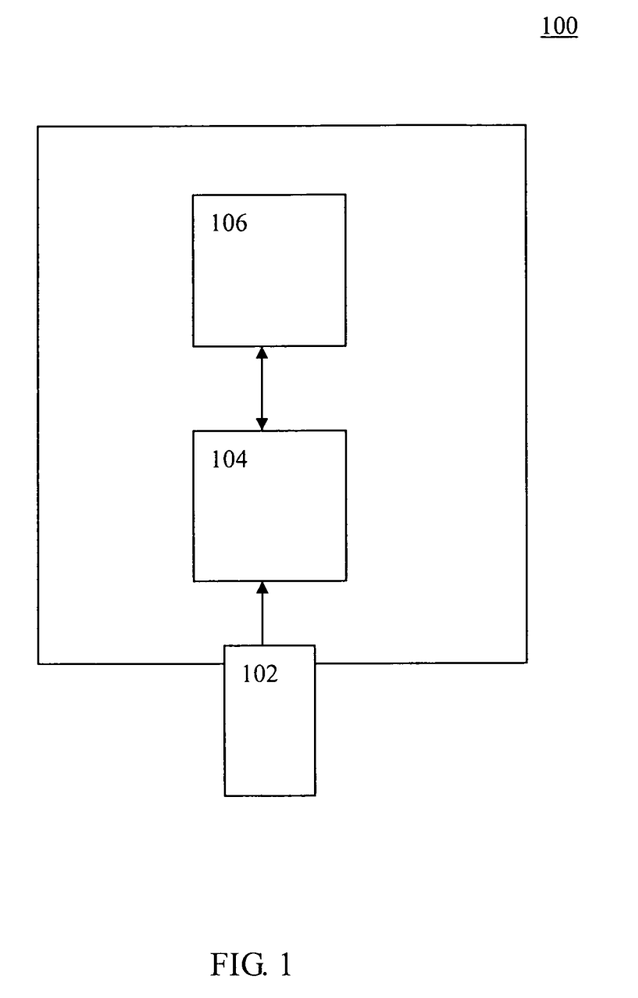
FIG. 1 illustrates a block diagram of an exemplary biological measuring device in accordance with one embodiment of the present invention.

Refer to FIG. 1. FIG. 1 illustrates a block diagram of an exemplary biological measuring device in accordance with one embodiment of the present invention. As an example, the biological measuring device of the present invention may be a blood glucose meter capable of measuring glucose from a blood sample. However, the biological measuring device of the present invention is not limited to the blood glucose meter. Instead, any device capable of measuring a medical analyte in an individual's body fluid sample is within the scope of the present invention.

As shown in FIG. 1, the biological measuring device of the present invention may include a code reader 104 and a memory 106 provided within the biological measuring device 100. Additionally, a test strip 102 may be inserted into the biological measuring device 100 to be electrically coupled to the code reader 104 when in use. In one embodiment of the present invention, the code reader 104 may include a plurality of metal pins to be electrically coupled to the test strip 102 when in operation so as to read information, such as coding information, from the test strip 102.

Furthermore, the code reader 104 of the present invention may be electrically coupled to the memory 106 so that information gathered from the test strip 102 by the code reader 104 may be stored in the memory 106. Additionally, the code reader 104 of the present invention may retrieve information from the memory 106 to work with the information collected from the test strip 102. Although FIG. 1 only shows the biological measuring device 100 consisted of the test strip 102, the code reader 104, and the memory 106, those skilled in the art would understand that the biological measuring device 100 of the present invention is not limited to these elements. For example, the biological measuring device 100 of the present invention may include a display, a plurality of buttons, a communication interface, etc. The detailed structures of which are not explained herein to prevent obscuring the focus of the present invention.

Figure 2A:
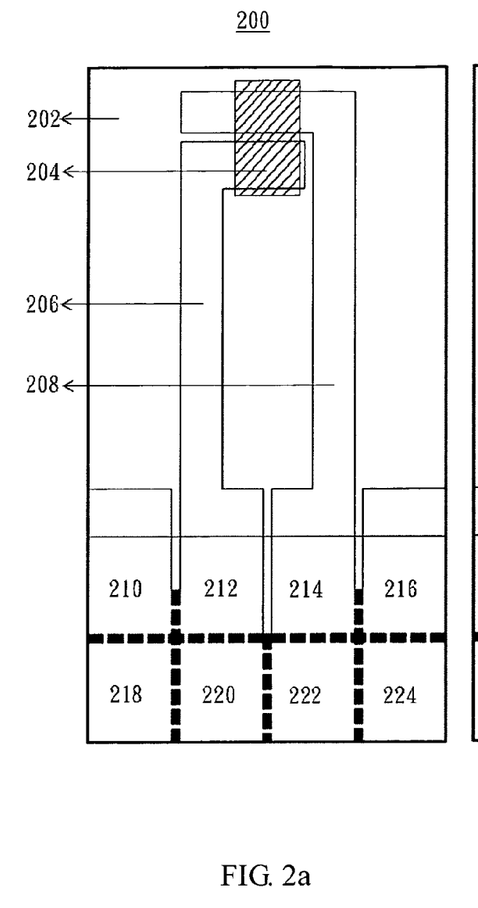
FIGS. 2a and 2b illustrate schematic diagrams of exemplary test strips in accordance with the first and second embodiments of the present invention.
Figure 2B:
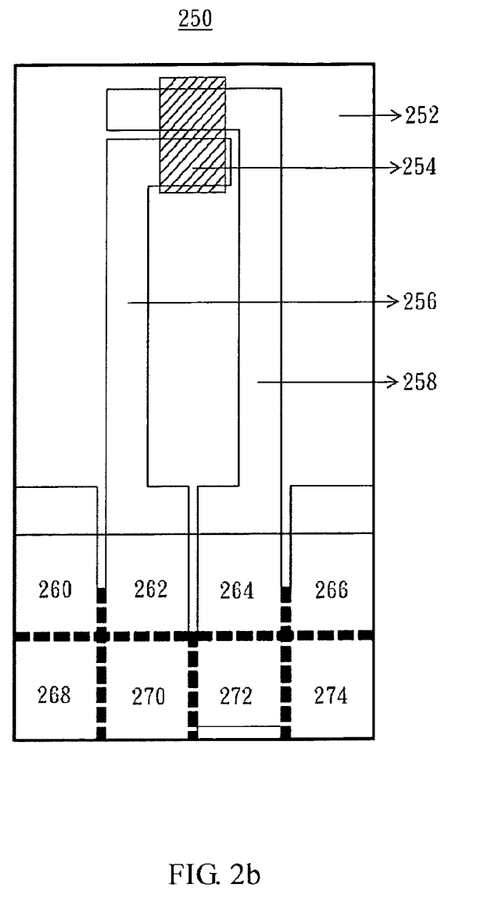

Refer to FIGS. 2a and 2b, which illustrate schematic diagrams of exemplary test strips in accordance with the present invention. In accordance with one embodiment of the present invention, the test strip 200 may include a substrate 202. The substrate 202 of the present invention may be made of an insulating material, such as polyethylene terephthalate (PET) or the like. In accordance with one embodiment of the present invention, at least two electrodes, such as any combination of a working electrode 206, a counter electrode (not shown), or a reference electrode 208, may be provided on the substrate 202. In one example, the working electrode 206 and the reference electrode 208 may be made of a conductive material, such as gold, palladium, silver, or carbon, as well known in the art, to form a reaction region 204 at one end of the substrate 202. In accordance with the present invention, the reaction region 204 may be applied with an enzyme so that when a test sample performs a chemical reaction with the enzyme at the reaction region 204, an electrical response may be generated from the test strip 200.

In one embodiment of the present invention, the other end of the substrate 202 may be provided with a plurality of contact pads. As shown in FIG. 2a, the substrate 202 may be provided with eight contact pads 210, 212, 214, 216, 218, 220, 222 and 224 at the bottom end. In accordance with the present invention, any one of the contact pads 210, 212, 214, 216, 218, 220, 222 and 224 on the test strip may be electrically coupled to the code reader, such as code reader 104 of FIG. 1, to transmit electrical response.

In accordance with another embodiment of the present invention, the test strip 250 may include a substrate 252. The substrate 252 of the present invention may be made of an insulating material, such as polyethylene terephthalate (PET) or the like. In accordance with one embodiment of the present invention, at least two electrodes, such as any combination of a working electrode 256, a counter electrode (not shown), or a reference electrode 258, may be provided on the substrate 252. The working electrode 256 and the reference electrode 258 may be made of a conductive material, such as gold, palladium, silver, or carbon, as well known in the art, to form a reaction region 254 at one end of the substrate 252. In another embodiment of the present invention, an additional counter electrode (not shown) may also be provided on the substrate 252 to form the reaction region 254. In accordance with the present invention, the reaction region 254 may be applied with an enzyme so that when a test sample performs a chemical reaction with the enzyme at the reaction region 254, an electrical response may be generated from the test strip 250.

In one embodiment of the present invention, the other end of the substrate 252 may be provided with a plurality of contact pads. As shown in FIG. 2b, the substrate 252 may be provided with eight contact pads 260, 262, 264, 266, 268, 270, 272 and 274 at the bottom end. In accordance with the present invention, any one of the contact pads 260, 262, 264, 266, 268, 270, 272 and 274 on the test strip 250 may be electrically coupled to the code reader, such as code reader 104 of FIG. 1, to transmit electrical response.

As can be seen from FIGS. 2a and 2b, the contact pads of the present invention may be arranged in two rows at one end of the test strip; however, those skilled in the art would understand that any shape or arrangement of the contact pads is within the scope of the present invention. Furthermore, in accordance with one embodiment of the present invention, the contact pads may be physically disconnected from one another so as to produce different conductivities among the contact pads. However, those skilled in the art would understand that the contact pads do not have to be disconnected from one another completely to produce different conductivities between any two contact pads. In another embodiment of the present invention, the contact pads may not be physically disconnected from one another and yet may produce different conductivities through other means so as to determine the coding information associated with the test strip. Such configurations of contact pads are also with the scope of present invention.

Additionally, as shown in FIGS. 2a and 2b, the contact pads provided on the test strips 200 and 250 may not be aligned at the end of the substrates 202 and 252. For example, contact pad 222 provided on test strip 200 is shown aligned at the end of the substrate 202, whereas contact pad 272 provided on test strip 250 is shown not aligned at the end of the substrate 252. In another embodiment of the present invention, more than one contact, pad may be aligned at the end of the substrate. In yet another embodiment of the present invention, more than one contact pad may not be aligned at the end of the substrate. In other words, in accordance with the present invention, the length of the contact pads provided on the test strip may vary so as to cause different movements as the test strip enters the code reader, thereby providing different combinations of coding information associated with the test strip.

Figure 2C:
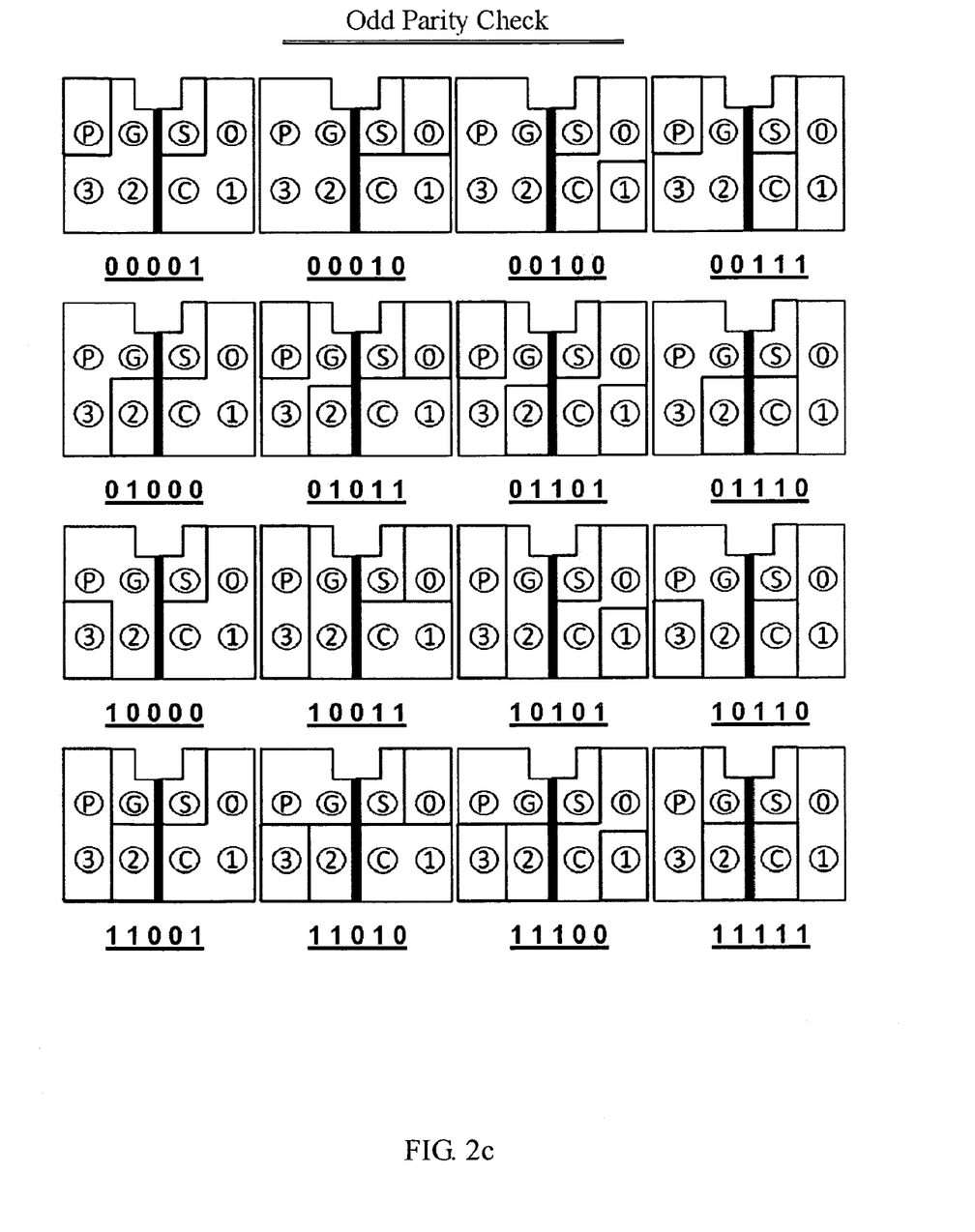
FIG. 2c illustrates schematic diagrams of exemplary test strips encoded with a variety of different information on the contact pads in accordance with one embodiment of the present invention.

Refer now to FIG. 2c in combination with FIG. 2a. FIG. 2c shows schematic diagrams of exemplary test strips encoded with different coding information on the contact pads in accordance with one embodiment of the present invention. As an example, the test strip shown in FIG. 2c is assigned with bits P, G, S, C, 0, 1, 2 and 3 to the eight contact pads. In one embodiment of the present invention, the code reader may read the coding information associated with the test strip by identifying the conductivity between, for example, bit 0 and bit C (common pin). If there is conductivity between bit 0 and C, then a logic value of 0 is the output. On the other hand, if there is no conductivity between bit 0 and bit C, then a logic value of 1 is the output. In another embodiment of the present invention, the code reader may read the coding information associated with the test strip by identifying the conductivity between, for example, bit 3 and bit G (ground). That is, if there is conductivity between bit 3 and bit G, then logic 0 is the output. On the other hand, if there is no conductivity between bit 3 and bit G, then logic 1 is the output. The code reader of the present invention may further determine the conductivity for bits 1, 2 and P with either bit G or C to obtain a combined result consisted of logic values of 0 and 1, which in turn may be used as the coding information associated with the test strip.

In one embodiment of the present invention, the physical connectivity between any two contact pads on the substrate may affect the conductivity between them. Take the test strip on the top left corner of FIG. 2c as an example. The test strip is manufactured such that P and S are isolated from any other contact pads. As a result, bit 0 has conductivity with bit C, outputting logic 0; bit 1 has conductivity with bit C, outputting logic 0; bit 2 has conductivity with bit G, outputting logic 0; bit 3 has conductivity with bit G, outputting logic 0; finally, bit P has no conductivity with bit G, outputting logic 1. As such, the coding information associated with such test strip is 00001. In accordance with the present invention, by varying the conductivity between any two contact pads, a greater combination of codes may be encoded onto the test strip such that the code reader may read the associated coding information when the test strip is placed properly within the code reader for calibration purpose.

In accordance with the present invention, P may be a parity bit assigned to one of the contact pads on the test strip so as to verify the correctness of the coding information associated with the test strip. As shown in FIG. 2c, in one embodiment of the present invention, a parity bit is assigned to one of the contact pads on the test strip. The code reader of the present invention that is used in combination with such test strip may be configured to perform an odd parity check. That is, if the coding information associated with the test strip outputs an odd number of logic 1, then the coding information is correct. On the other hand, if the coding information associated with the test strip outputs an even number of logic 1, then the coding information is not incorrect. For example, the conductivity for bits 0, 1, 2, 3 and P with G or C shown in FIG. 2c causes the test strip to output one, three, or five logic 1s, regardless of the location of "1". That is, the coding information associated with the test strip may be "00001", "00111", or "11111", etc. In such case, P may be referred to as an odd parity bit, and the odd parity check passes. In other words, the coding information associated with the test strip is correct.

Figure 2D:
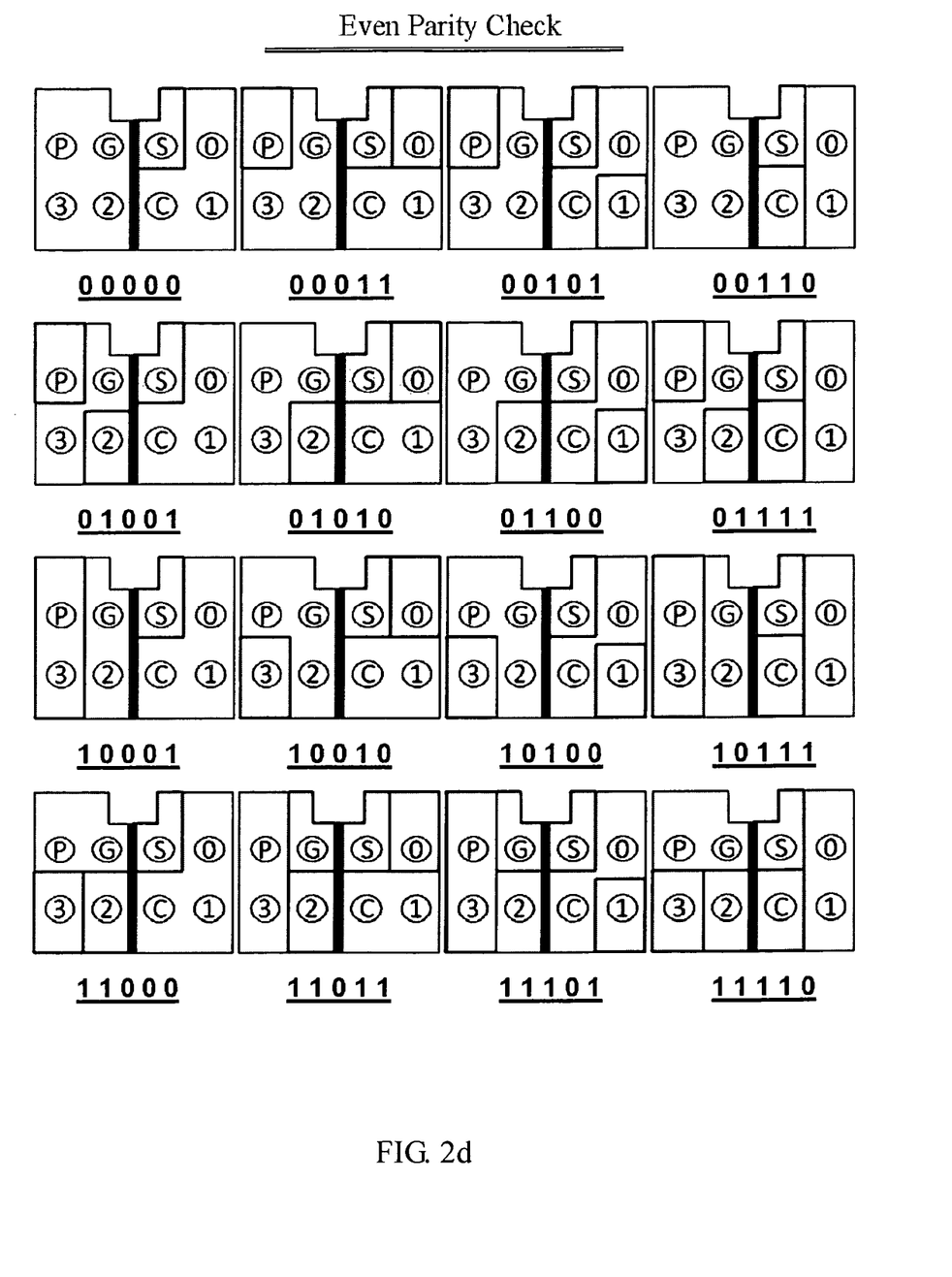
FIG. 2d illustrates schematic diagrams of exemplary test strips encoded with a variety of different information on the contact pads in accordance with another embodiment of the present invention.

In another embodiment of the present invention, the code reader that is used in combination with the test strip assigned with a parity bit may be configured to perform an even parity check That is, if the coding information associated with the test strip outputs an even number of logic 1, then the coding information is correct. On the other hand, if the coding information associated with the test strip outputs an odd number of logic 1, then the coding information is incorrect. For example, the conductivity for bits 0, 1, 2, 3 and P with G or C shown in FIG. 2d causes the test strip to output zero, two, or four logic 1s, regardless of the location of "1". That is, the coding information associated with the test strip may be "00000", "00011", or "01111", etc. In such case, P may be referred to as an even parity bit, and the even parity check passes. In other words, the coding information associated with the test strip is correct.

In accordance with the present invention, assigning an odd or even parity bit to the contact pads on the test strip provides a way to verify the correctness of the reading of the coding information associated with the strip, thereby reducing the risk of reading wrong coding information associated with the test strip due to manufacturing defects, such as scratches or dusts. However, without the parity bit, information can still be made with the contact pads through the different conductivity among the contact pads to distinguish one test strip from another, and thus to calibrate the biological measuring device in accordance with the present invention. Those skilled in the art should understand that the parity bit is not limited to be assigned to only the contact pad shown in FIGS. 2c and 2d; instead, the parity bit may be assigned to any of the contact pads on the test strip in accordance with the present invention.

Figure 3A:
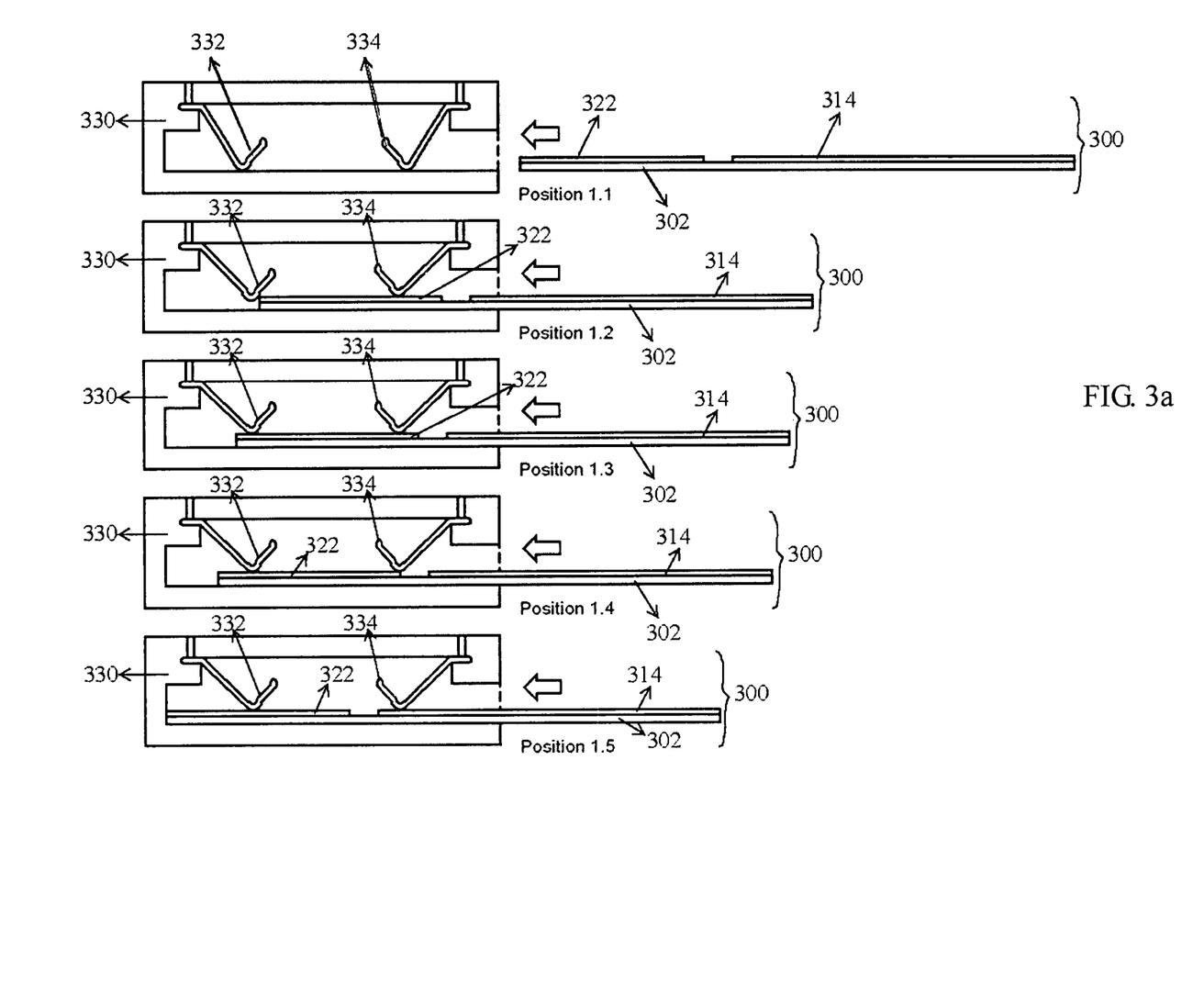
FIGS. 3a and 3b illustrate schematic diagrams of exemplary biological measuring devices in operations in accordance with the first and second embodiments of the present invention.
Figure 3B:
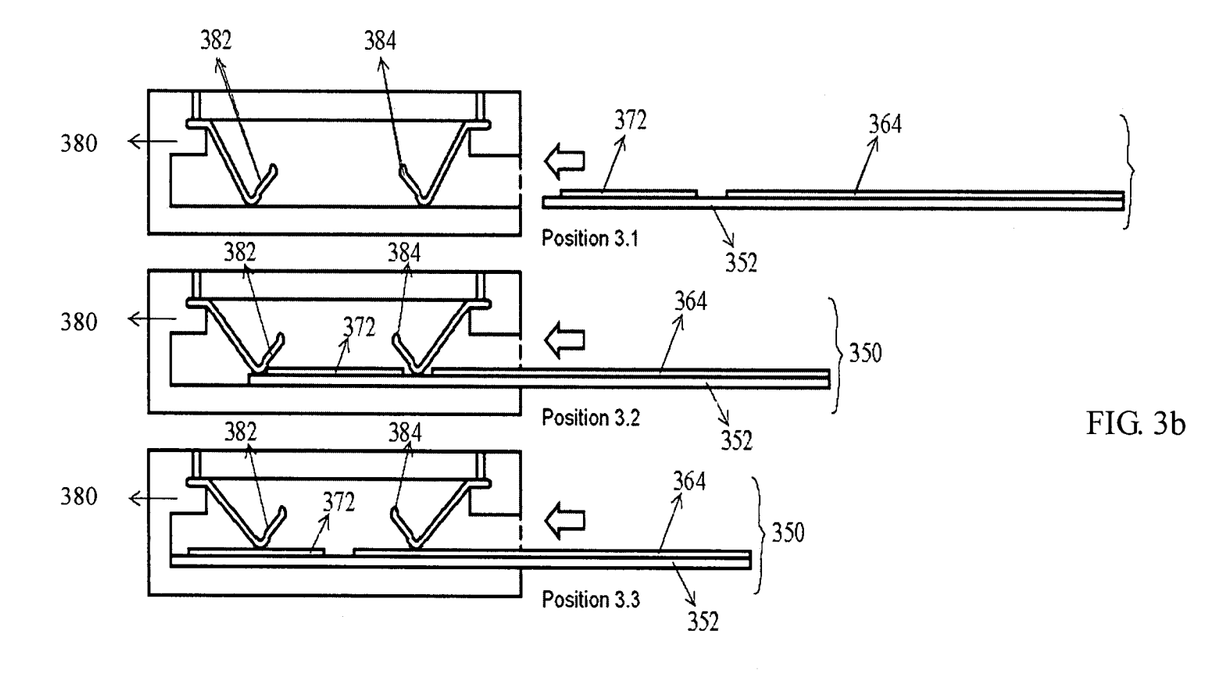

Refer now to FIGS. 3a and 3b, which illustrate schematic diagrams of exemplary biological measuring devices in operations in accordance with the present invention. In accordance with the present invention, the length of one of the contact pads and/or the alignment of one of the contact pads with the substrate of the test strip may determine the coding information associated with the test strip.

In one embodiment of the present invention, as shown in position 1.1 of FIG. 3a, the contact pad 322 provided on the test strip 300 is aligned with one end of the substrate 302. As the test strip 300 moves into the code reader 330 as shown in position 1.2 of FIG. 3a, the contact pad 322 may first become in contact with the metal pin 334 only. As the test strip 300 moves further into the code reader 330 as shown in position 1.3 of FIG. 3a, the contact pad 322 may then become in contact with both the metal pins 332 and 334.

In accordance with the present invention, the contact pad 322 being in contact with both the metal pins 332 and 334 at the same time, as shown in position 1.3 of FIG. 3a, may be caused by the length of the first contact pad, by the alignment of the first contact pad with one end of the substrate, by the gap between the first metal pin and the second metal pin provided on the code reader, or by any combination thereof. In the scenario shown in position 1.3 of FIG. 3a, the first contact pad is aligned with one end of the substrate. Additionally, the gap between the first metal pin and the second metal pin is smaller than the length of the first contact pad. As such, the metal pins 332 and 334 are electrically coupled to the first contact pad 322 at the same time as the test strip 300 moves into the code reader 330.

Then, as shown in position 1.4 of FIG. 3a, the contact pad 322 may remain in contact with the metal pin 332, as the metal pin 334 comes off the contact pad 322 before the test strip 300 reaches its final position and allows the metal pins 334 to be in contact with the contact pad 314 as shown in position 1.5 of FIG. 3a. After the first contact pad 322 and the second contact pad 314 move into their final position to be electrically coupled to the first metal pin 332 and the second metal pin 334, respectively, the test strip 300 may now be placed still in the code reader 330 for proper reading of a test sample.

In accordance with one embodiment of the present invention, as shown in FIG. 3a, the gap between the metal pins 332 and 334 provided within the code reader 330 is smaller than the length of the contact pad 322 so that as the test strip 300 moves to the proper position within the code reader 330, the metal pins 332 and 334 may be both contacting the contact pad 322 at a given point in time.

In accordance with one embodiment of the present invention, when the metal pins 332 and 334 both move onto the same contact pad, such as contact pad 322, the metal pins 332 and 334 as well as the contact pad 322 are electrically coupled to one another. At this time, an electrical conductivity exists between the metal pins 332 and 334 through the contact pad 322. Consequently, the circuit formed by the metal pins 332 and 334 as well as the contact pad 322 is known as a closed circuit by those ordinarily skilled in the art. As such, the test strip 300 may be referred to as being in a closed circuit movement. On the other hand, when the metal pins 332 and 334 move on different contact pads, such as contact pads 322 and 314, respectively, the metal pins 332 and 334 are not electrically coupled to each other. At this time, no conductivity exists between the metal pins 332 and 334 through either the contact pad 322 or the contact pad 314. Consequently, the circuit formed by the metal pins 332 and 334 as well as the contact pad 322 is known as an open circuit by those ordinarily skilled in the art. Additionally, the circuit formed by the metal pins 332 and 334 as well as the contact pad 314 is also known as an open circuit by those ordinarily skilled in the art. As such, the test strip 300 may be referred to as being in an open circuit movement. In other words, FIG. 3a illustrates a movement of the test strip 300 that includes both an open circuit movement and a closed circuit movement from the point when the test strip 300 enters the code reader 330 to the point when the test strip 330 is properly set within the code reader 330 and ready for code reading.

More specifically, FIG. 3a illustrates a sequence of movement of the test strip 300, including an open circuit movement, a closed circuit movement, and back to an open circuit movement before the test strip 300 is properly positioned in the code reader 330 for reading of the coding information associated with the test strip 300. In accordance with the present invention, the code reader 330 may be capable of reading the coding information associated with the test strip 300 based on the sequence of the movement of the test strip 300 in addition to reading the coding information associated with the test strip 300 when the test strip 300 is properly set still within the code reader 330.

In another embodiment of the present invention, as shown in position 3.1 of FIG. 3b, the contact pad 372 provided on the test strip 350 is not aligned with one end of the substrate 352. In other words, a space is left between one end of the substrate 352 and one end of the contact pad 372. As the test strip 350 moves into the code reader 380 as shown in position 3.2 of FIG. 3b, the contact pad 372 may become electrically coupled to the metal pins 384 and 382 sequentially before the test strip 300 reaches its final position and allow the metal pin 384 to be in contact with the contact pad 364 as shown in position 3.3 of FIG. 3b.

In accordance with one embodiment of the present invention, as shown in FIG. 3b, because of the length of the contact pad 372 and/or the lack of alignment of the contact pad 372 to the substrate 352, there may not be a point in time when the metal pins 382 and 384 both move on the same contact pad, such as contact pad 372. In other words, the metal pins 382 and 384 are not electrically coupled to the contact pad 372 at the same time as the test strip 350 moves into the code reader 380. Since no conductivity exists between the metal pins 332 and 334 through either the contact pad 372 or the contact pad 364, the circuit formed by the metal pins 332 and 334 as well as the contact pad 372 is known as an open circuit by those ordinarily skilled in the art. The circuit formed by the metal pins 332 and 334 as well as the contact pad 364 is also known as an open circuit by those ordinarily skilled in the art. As such, there may only be an open circuit movement from the point when the test strip 350 enters the code reader 380 to the point when the test strip 350 is properly set within the code reader 380 and ready for code reading.

In accordance with the present invention, the code reader 380 may be capable of reading the coding information associated with the test strip 350 based on the sequence of the movement of the test strip 350, or lack of sequence as is the case in FIG. 3b, in addition to reading the coding information associated with the test strip 350 when the test strip 350 is properly set still within the code reader 380. That is, the code reader of the present invention may recognize more coding information associated with the test strip based on the movement of the test strip as a result of the length of the contact pad provided on the test strip and/or the alignment of the contact pad with one end of the test strip.

Figure 4:
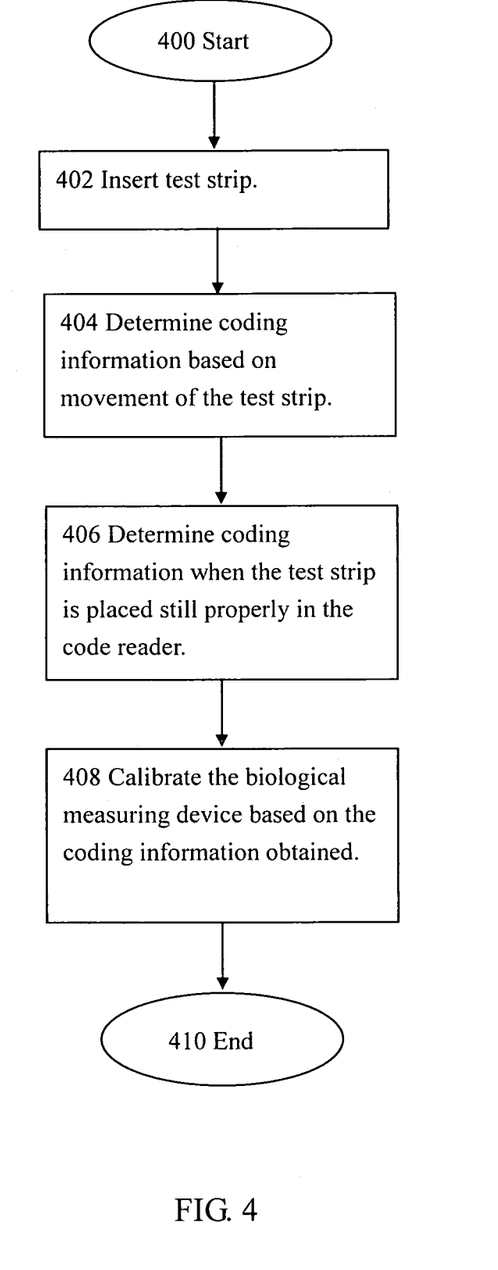
FIG. 4 illustrates a flow chart of an exemplary method of determining coding information associated with a test strip adapted for use with a biological measuring device in accordance with one embodiment of the present invention.

Refer to FIG. 4, which illustrates a flow chart of an exemplary method of determining coding information associated with a test strip adapted for use with a biological measuring device in accordance with one embodiment of the present invention. As shown in FIG. 4, the method starts at step 400. At step 402, the present method may insert a test strip, such as the test strip 102 of FIG. 1, into a code reader, such as the code reader 104 of FIG. 1, provided in a biological measuring device. As mentioned above, the biological measuring device of the present invention may be a blood glucose meter capable of measuring glucose from a blood sample. However, the biological measuring device of the present invention is not limited to the blood glucose meter. Instead, any device capable of measuring a medical analyte in an individual's body fluid sample is within the scope of the present invention.

Then, at step 404, for example, the code reader of the present invention may determine the coding information associated with the test strip inserted based on a movement of the test strip. In one embodiment of the present invention, the movement of the test strip may include, for example, a sequence of an open circuit movement, a closed circuit movement and back to an open circuit movement, as described in details in FIG. 3a above. In another embodiment of the present invention, the movement of the test strip may include, for example, only an open circuit movement, as described in details in FIG. 3b above. In accordance with the present invention, different movements of the test strip may result in different coding information being read by the code reader.

Then, optionally, at step 406, the code reader of the present invention may determine the coding information associated with the test strip when the test strip is placed still in the code reader. That is, for example, when the contact pads 322 and 314 are electrically coupled to the metal pins 332 and 334, respectively, in FIG. 3a, or when the contact pads 372 and 364 are electrically coupled to the metal pins 382 and 384, respectively, in FIG. 3b.

At step 408, the coding information obtained from the test strip is used to calibrate the biological measuring device before a user uses it to obtain a test result. The present method ends at step 410.

Figure 5:
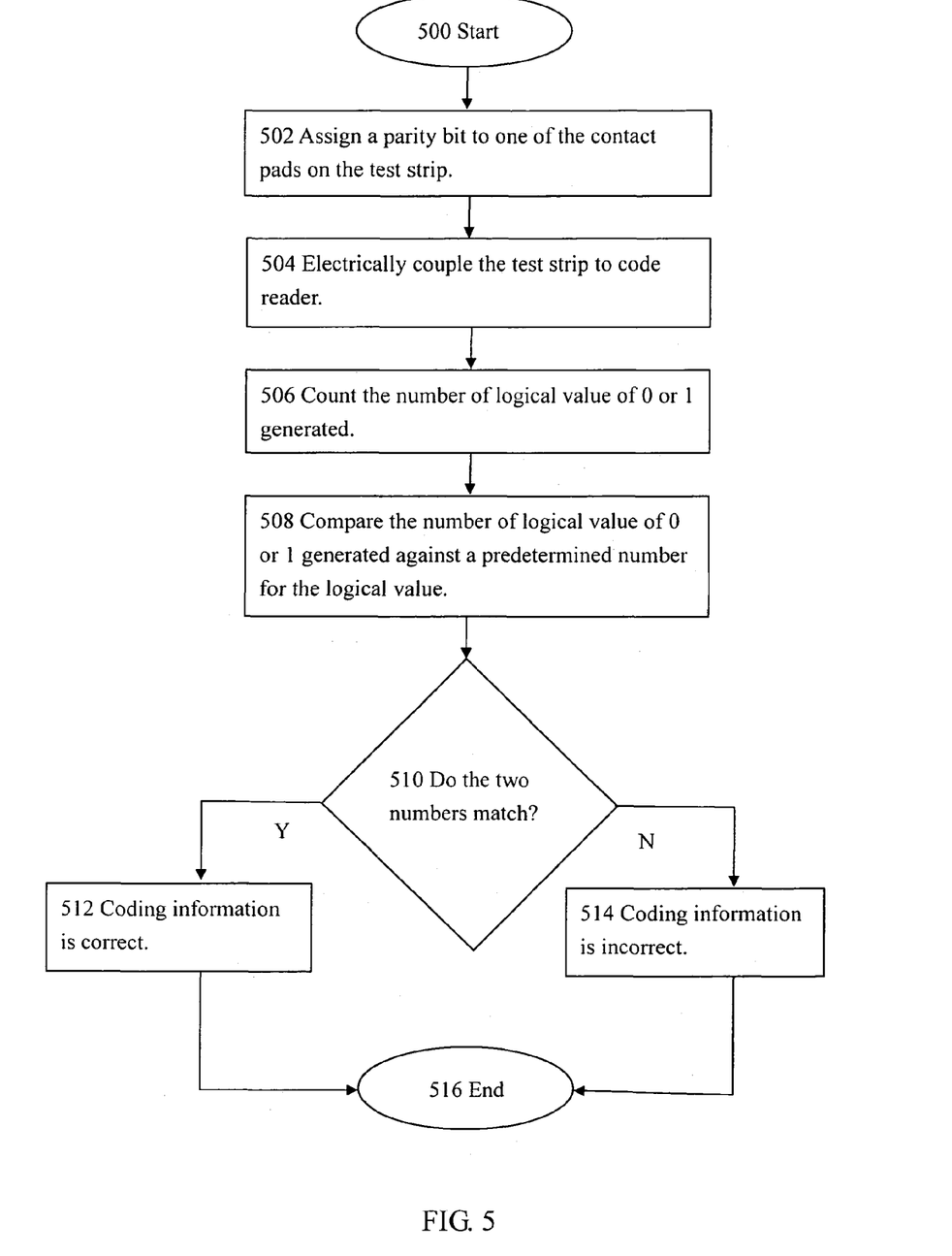
FIG. 5 illustrates a flow chart of an exemplary method of verifying coding information associated with a test strip adapted for use with a biological measuring device in accordance with one embodiment Of the present invention.

Refer now to FIG. 5, which illustrates a flow chart of an exemplary method of verifying coding information associated with a test strip adapted for use with a biological measuring device in accordance with one embodiment of the present invention. As shown in FIG. 5, the method may start at step 500. At step 502, the present method may assign a parity bit to one of the contact pads on the test strip. For example, the parity bit may be assigned to the contact pad 210 on the test strip 200 in FIG. 2a. Then, at step 504, the test strip may be electrically coupled to the code reader as the test strip is pushed into the code reader. When the test strip is properly set within the code reader, the conductivity among the contact pads may generate logical values of zero and one to be read by the code reader.

At step 506, in one embodiment of the present invention, the code reader may count the number of logical value of one generated by the test strip. Then, at step 508, the code reader may compare the number of logical value of one generated by the test strip against a predetermined number set for the logical value. For example, the predetermined number may be any even number. That is, the code reader may perform an even parity check at step 508. Therefore, if the number of logical value of one generated by the test strip is two, then, at step 510, there is a match. As a result, the coding information obtained is deemed correct at step 510.

However, if the number of logical value of one generated by the test strip is one, then at step 510, there is no match. As a result, the coding information obtained is deemed incorrect. In such case, the biological measuring device of the present invention may alert the user and/or request the user to insert the test strip again before the biological measuring device may be used properly.

In another embodiment of the present invention, at step 508, the code reader may compare the number of logical value of one generated by the test strip against a predetermined number set for the logical value. For example, the predetermined number may be any odd number. That is, the code reader may perform an odd parity check at step 508. Therefore, if the number of logical value of one generated by the test strip is three, then, at step 510, there is a match. As a result, the coding information obtained is deemed correct at step 510.

However, if the number of logical value of one generated by the test strip is two, then at step 510, there is no match. As a result, the coding information obtained is deemed incorrect. In such case, the biological measuring device of the present invention may alert the user and/or request the user to insert the test strip again before the biological measuring device may be used properly. The present invention ends at step 516.

In accordance with the present invention, the code reader's capability to read the coding information associated with the test strip as the test strip moves into the code reader increases the amount of information that may be encoded on the test strip without changing the existing structure and configuration of the biological measuring device and the test strip. For example, an arrangement of the eight contact pads with 2 rows of 4 contact pads provided on the substrate may exhibit 16 ($=2^4$) codes in any given test strip originally. By reading the code information based on the movement of the test strip before the test strip is placed still in relation to the code reader of the present invention, the code information carried by the test strip may increase to, for example, 81 ($=1\times2^0+4\times2^1+6\times2^2+4\times2^3+1\times2^4$) codes without increasing the number of contact pads on the substrate. Furthermore, by assigning a parity bit to one of the contact pads on the test strip, the correctness of the coding information associated with the test strip read by the cod ready may be improved.

While the invention has been described in conjunction with exemplary preferred embodiments, it is to be understood that many alternatives, modifications, and variations will be apparent to those skilled in the art in light of the foregoing description. Accordingly, the present invention embraces all such alternatives, modifications, and variations. All matters set forth herein or shown in the accompanying drawings are to be interpreted in an illustrative and non-limiting sense.

What is claimed is:

1. A biological measuring device with auto coding capabilities, said device comprising:
    a test strip having a substrate and at least a first contact pad and a second contact pad provided on said substrate; and
    a code reader having at least a first metal pin and a second metal pin to couple to said first contact pad and said second contact pad to obtain coding information associated with said test strip,
    wherein said code reader is capable of reading said coding information based on a movement of said test strip before said test strip is placed still in relation to said code reader for a proper reading of a sample, and wherein a length of said first or second contact pad provided on said substrate determines said movement.

2. The device of claim 1, wherein said movement includes an open circuit movement when said first and second metal pins do not contact said first contact pad at the same time as said test strip moves towards said code reader.

3. The device of claim 1, wherein said movement includes a closed circuit movement when said first and second metal pins contact said first contact pad at the same time as said test strip moves towards said code reader.

4. The device of claim 1, wherein said code reader is capable of reading said coding information based on a sequence of an open circuit movement and a closed circuit movement, wherein said closed circuit movement is a movement when said first and second metal pins contact said first contact pad at the same time as said test strip moves towards said code reader, and wherein said open circuit movement is a movement when said first and second metal pins do not contact said first contact pad at the same time as said test strip moves towards said code reader.

5. The device of claim 1, wherein said first contact pad is physically disconnected from said second contact pad on said substrate.

6. The device of claim 1, wherein a gap between said first metal pin and said second metal pins is larger than said length of said first contact pad.

7. The device of claim 1, wherein a gap between said first metal pin and said second metal pin is smaller than said length of said first contact pad.

8. The device of claim 1, wherein said first contact pad is physically connected to said second contact pad on said substrate.

9. The device of claim 1, wherein said test strip has a third contact pad assigned with a parity bit to verify said coding information.

10. A biological measuring device adapted for use with a test strip, wherein said test strip has at least a first contact pad and a second contact pad, and wherein said first contact pad has a first length and said second contact pad has a second length, said device comprising:
    a code reader having at least a first metal pin and a second metal pin,
    wherein said code reader is capable of reading coding information associated with said test strip based on a movement of said test strip before said test strip is placed still in relation to said code reader for a proper reading of a sample, and wherein said first length or said second length determines said movement.

11. The device of claim 10, wherein said movement includes an open circuit movement when said first and second metal pins do not contact said first contact pad at the same time as said test strip moves towards said code reader.

12. The device of claim 10, wherein said movement includes a closed circuit movement when said first and second metal pins contact said first contact pad at the same time as said test strip moves towards said code reader.

13. The device of claim 10, wherein said code reader is capable of reading said coding information based on a sequence of an open circuit movement and a closed circuit movement, wherein said closed circuit movement is a movement when said first and second metal pins contact said first contact pad at the same time as said test strip moves towards said code reader, and wherein said open circuit movement is a movement when said first and second metal pins do not contact said first contact pad at the same time as said test strip moves towards said code reader.

14. The device of claim 10, wherein said test strip has a third contact pad assigned with a parity bit to verify said coding information.

15. The biological measuring device of claim 10, wherein said first length is equal to said second length.

16. A test strip adapted for use with a biological measuring device, said biological measuring device comprising a code reader having at least a first metal pin and a second metal pin, said test strip comprising:
    a substrate;
    a reaction region formed by at least a first electrode and a second electrode provided on said substrate at one end, said reaction region is applied with an enzyme so that an electrical response is generated when said enzyme and a test sample form a chemical reaction, and
    at least a first contact pad and a second contact pad provided on said substrate at the other end to couple to said first and second metal pins to output coding information associated with said test strip,
    wherein a length of said first or second contact pad determines a movement of said test strip before said test strip is placed still in relation to said code reader for a proper reading of said test sample, and wherein a gap between said first metal pin and said second metal pin is larger or smaller than said length of said first or second contact pad.

17. The test strip of claim 16, wherein said first contact pad is physically connected to said second contact pad on said substrate.

18. The test strip of claim 16, wherein said first contact pad is physically disconnected from said second contact pad on said substrate.

19. The test strip of claim 16, further having a third contact pad assigned with a parity bit to verify said coding information.

20. A method of reading coding information associated with a test strip adapted for use with a biological measuring device, said test strip having a substrate and at least a first contact pad and a second contact pad provided on said substrate, and said biological measuring device comprising a code reader having at least a first metal pin and second metal pin, said method comprising:
 inserting said test strip into said code reader; and
 reading said coding information based on a movement of said test strip before said test strip is placed still in relation to said code reader for a proper reading of a sample,
 wherein said movement includes an open circuit movement and a closed circuit movement.

21. The method of claim 20, wherein said open circuit movement and said closed circuit movement are determined by a length of said first or second contact pads on said test strip.

22. The method of claim 20, wherein said first contact pad is physically disconnected from said second contact pad on said substrate.

23. The method of claim 20, wherein a gap between said first metal pin and said second metal pin is smaller than said length of said first contact pad to cause a sequence of said open and closed circuit movements as said test strip moves towards said code reader.

24. The method of claim 20, wherein a gap between said first metal pin and said second metal pin is larger than said length of said first contact pad to cause only said open circuit movement as said test strip moves towards said code reader.

25. The method of claim 20, further comprising assigning a parity bit to a third contact pad provided on said test strip to verify said coding information.

26. A method of verifying coding information associated with a test strip adapted for use with a biological measuring device, said test strip having a substrate and a plurality of contact pads provided on said substrate, and said biological measuring device comprising a code reader having a plurality of metal pins corresponding to said plurality of contact pads, said method comprising:
 assigning a parity bit to one of said plurality of contact pads;
 determining said coding information by counting the number of a logical value generated when said plurality of contact pads are electrically coupled to said plurality of corresponding metal pins;
 comparing said number of said logical value against a predetermined number for said logical value, and if said number of logical value matches said predetermined number for said logical value, then said coding information is correct.

27. The method of claim 26, further comprising determining said coding information based on a movement of said test strip before said test strip is placed still in relation to said code reader for a proper reading of a sample, wherein said movement includes an open circuit movement, a closed circuit movement or a combination of said open and closed circuit movements.

28. The method of claim 26, wherein said logical value is zero or one.

29. A test strip adapted for use with a biological measuring device, said biological measuring device comprising a code reader having a plurality of metal pins, said test strip comprising:
 a substrate;
 a reaction region formed by at least a first electrode and a second electrode provided on said substrate at one end, said reaction region is applied with an enzyme so that an electrical response is generated when said enzyme and a test sample form a chemical reaction, and
 a plurality of contact pads provided on said substrate, wherein a first and second contact pads of said plurality of contact pads are provided on said substrate at the other end to couple to a respective metal pin to output coding information associated with said test strip, and wherein a third contact pad of said plurality of contact pads is assigned with a parity bit to verify said coding information.

30. The test strip of claim 29, wherein a length of said first or second contact pad determines a movement of said test strip before said test strip is placed still in relation to said code reader for a proper reading of said test sample.

31. The test strip of claim 30, wherein a gap between said first metal pin and said second metal pin is larger than said length of said first or second contact pad.

32. The test strip of claim 30, wherein a gap between said first metal pin and said second metal pin is smaller than said length of said first or second contact pad.

33. The test strip of claim 29, wherein said first contact pad is physically connected to said second contact pad on said substrate.

34. The test strip of claim 29, wherein said first contact pad is physically disconnected from said second contact pad on said substrate.

35. A biological measuring device adapted for use with a test strip, said test strip having at least a first, a second and a third contact pads, said device comprising:
 a code reader having at least a first metal pin and a second metal pin,
 wherein said code reader is capable of reading coding information associated with said test strip based on a movement of said test strip before said test strip is placed still in relation to said code reader for a proper reading of a sample, and
 wherein said code reader verifies said coding information using a parity bit assigned to said third contact pad provided on said test strip.

36. The device of claim 35, wherein said movement includes an open circuit movement when said first and second metal pins do not contact said first contact pad at the same time as said test strip moves towards said code reader.

37. The device of claim 35, wherein said movement includes a closed circuit movement when said first and second metal pins contact said first contact pad at the same time as said test strip moves towards said code reader.

38. The device of claim 35, wherein said code reader is capable of reading said coding information based on a sequence of an open circuit movement and a closed circuit movement, wherein said closed circuit movement is a movement when said first and second metal pins contact said first contact pad at the same time as said test strip moves towards said code reader, and wherein said open circuit movement is a movement when said first and second metal pins do not contact said first contact pad at the same time as said test strip moves towards said code reader.

* * * * *